(12) United States Patent
Matsumoto et al.

(10) Patent No.: US 8,821,903 B2
(45) Date of Patent: Sep. 2, 2014

(54) METHOD FOR PRODUCING A VESICLE COMPOSITION

(75) Inventors: Hiromasa Matsumoto, Tokyo (JP); Sumie Matsuoka, Tokyo (JP); Hidetake Nakamura, Wakayama (JP); Makio Tetsu, Tokyo (JP); Fumiko Sazanami, Tokyo (JP); Shunsuke Watanabe, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/383,943

(22) PCT Filed: Jul. 8, 2010

(86) PCT No.: PCT/JP2010/004450
§ 371 (c)(1),
(2), (4) Date: Jan. 13, 2012

(87) PCT Pub. No.: WO2011/007525
PCT Pub. Date: Jan. 20, 2011

(65) Prior Publication Data
US 2012/0114721 A1    May 10, 2012

(30) Foreign Application Priority Data
Jul. 15, 2009  (JP) ................... P2009-166496

(51) Int. Cl.
| | | |
|---|---|---|
| *A61K 8/02* | (2006.01) | |
| *A61K 8/18* | (2006.01) | |
| *A61Q 5/00* | (2006.01) | |
| *A61K 8/14* | (2006.01) | |
| *A61K 8/36* | (2006.01) | |
| *A61K 8/41* | (2006.01) | |

(52) U.S. Cl.
CPC ... *A61K 8/14* (2013.01); *A61Q 5/00* (2013.01); *A61K 8/361* (2013.01); *A61K 8/41* (2013.01)
USPC .......................................... 424/401; 424/70.1

(58) Field of Classification Search
USPC ................................. 424/70.1, 401
See application file for complete search history.

(56) References Cited

U.S. PATENT DOCUMENTS

| | | |
|---|---|---|
| 5,137,725 A | 8/1992 | Handjani et al. |
| 5,476,649 A | 12/1995 | Naito et al. |
| 6,432,420 B2 | 8/2002 | Ellis et al. |
| 2001/0008631 A1* | 7/2001 | Ellis et al. ..................... 424/400 |
| 2005/0256040 A1* | 11/2005 | Bredesen et al. ............... 514/12 |
| 2006/0067893 A1* | 3/2006 | Koshti et al. .................... 424/59 |
| 2006/0198807 A1* | 9/2006 | Morioka .................... 424/70.22 |
| 2008/0050330 A1* | 2/2008 | Ishino ........................ 424/70.12 |
| 2009/0023003 A1 | 1/2009 | Kunishima |
| 2009/0047231 A1 | 2/2009 | Sazanami et al. |

FOREIGN PATENT DOCUMENTS

| | | |
|---|---|---|
| FR | 2 597 345 A1 | 10/1987 |
| JP | 63-501639 A | 6/1988 |
| JP | 4-173719 A | 6/1992 |
| JP | 2002-516831 A | 6/2002 |
| JP | 2004-67534 A | 3/2004 |
| JP | 2007-15986 A | 1/2007 |
| JP | 2007-176923 A | 7/2007 |
| WO | WO 2006/080157 A1 | 8/2006 |
| WO | WO 2007/064042 A1 * | 6/2007 |

OTHER PUBLICATIONS

International Preliminary Report of Patentability and translation of Written Opinion of the International Searching Authority for Application No. PCT/JP2010/004450 dated Feb. 16, 2012.
International Search Report for Application No. PCT/JP2010/004450 dated Nov. 9, 2010.
Sole et al., "Optimization of Nano-emulsion Preparation by Low-Energy Methods in an Ionic Surfactant System," Langumuir, vol. 22, No. 20, 2006, pp. 8326-8332. (Published online Aug. 31, 2006).
Notification of First Office Action for corresponding Chinese Patent Application No. 201080031290.6, dated Oct. 8, 2012.

* cited by examiner

*Primary Examiner* — Blessing M Fubara
(74) *Attorney, Agent, or Firm* — Birch, Stewart, Kolasch & Birch, LLP

(57) ABSTRACT

The present invention is a method for producing a vesicle composition having an aqueous phase as a continuous phase, the method including a step of dissolving an oil phase containing component (A) a branched fatty acid having a predetermined structure; component (B) a tertiary amine having a predetermined structure; and component (C) an organic acid having 1 to 10 carbon atoms at a temperature that is equal to or higher than a melting point of the oil phase, and a step of carrying out mixing while adding the aqueous phase to the oil phase which is dissolved.

2 Claims, No Drawings

METHOD FOR PRODUCING A VESICLE COMPOSITION

TECHNICAL FIELD

The present invention relates to a method for producing a vesicle composition.

BACKGROUND ART

In recent years the use of perms, hair coloring, bleaching, and so on has become popular. On the other hand, hair damage accompanying these chemical treatments has become a problem. Conventionally, a hair cosmetic such as a rinse, a conditioner or a treatment is used in order to improve the feel of hair after shampooing, and further improvement of performance has been desired from the viewpoint of alleviating hair damage.

Patent Document 1 proposes a hair cosmetic containing a specific branched fatty acid as a technique for repairing or suppressing hair damage and providing good texture.

Patent Documents 2 and 5 disclose hair cosmetics that repair or suppress hair damage and fatigue failure due to chemical treatments, drying with a dryer and daily hair care activity, and can provide desirable softness and a supple feel from moistening to drying. These hair cosmetics contain a specific tertiary amine or a salt thereof, a specific aromatic alcohol, a specific branched fatty acid or a salt thereof and water. It is stated that as a result these hair cosmetics are excellent in terms of softness, smoothness, moist feel, suppleness, and the like after application to hair and drying.

Furthermore, Patent Document 3 discloses a lipid dispersion composition for the purpose of efficiently repairing hair damage, and a hair cosmetic containing the same. The lipid dispersion composition of Patent Document 3 is produced by dispersing a di-long chain alkyl quaternary ammonium salt type cationic surfactant, a sterol, and a quaternary ammonium salt type cationic surfactant having a branched fatty acid amide structure in a dispersion medium containing 50 wt % or more of a polyol.

Furthermore, Patent Document 4 discloses a hair treatment composition containing cholesterol, a basic amino acid, a fatty acid, and a multilamellar vesicle dispersion that is stabilized by a nonionic surfactant, and a hair treatment composition such as a shampoo or a conditioner containing multilamellar vesicle dispersion, for the purpose of repairing and preventing hair damage. It is stated that this treatment composition specifically promotes penetration of some hair-treatment effective materials into hair fibers.

As one method for producing an emulsion composition, a phase inversion emulsification method or a liquid crystal emulsification method is known. The phase inversion emulsification method is a method in which emulsification is carried out while adding an aqueous phase to an oil phase. The liquid crystal emulsification method is a method in which emulsification is carried out while adding an aqueous phase to a liquid crystal phase. For example, in Non-Patent Document 1, a fine emulsion having an average particle size of no more than 1 μm is formed by utilizing a great reduction in the oil/water interfacial tension near the phase inversion point when carrying out emulsification while adding an aqueous phase to an oil phase.

RELATED DOCUMENTS

Patent Documents

[Patent Document 1] Japanese Patent Publication NO. JP-A-4-173719
[Patent Document 2] Japanese Patent Publication NO. JP-A-2007-176923
[Patent Document 3] Japanese Patent Publication NO. JP-A-2007-015986
[Patent Document 4] Published Japanese Translation of a PCT application NO. JP-A-2002-516831
[Patent Document 5] US Patent Publication NO. US-A-2009/0047231

Non-Patent Documents

[Non-Patent Document 1] Langmuir 2006, 22, 8326-8332

DISCLOSURE OF THE INVENTION

In accordance with the above-mentioned related techniques, it has been proposed that a branched fatty acid or salt thereof or a tertiary amine or salt thereof is used in combination with a specific branched fatty acid or salt thereof and, furthermore, that a quaternary ammonium salt type cationic activator is used in combination with a branched fatty acid, from the viewpoint of imparting softness, smoothness, moist feel, and the like.

At the same time, there is a desire for optimization of the content of such effective components and the formulation mixture. However, as a production method a conventional method has been carried out, and there has been no mention of improvement of the production method.

In the technique described in Patent Document 4, multilamellar vesicles are formed by mixing cholesterol as an essential component. That is, a vesicle structure is formed due to the interposition of a specific lipid such as a sterol. However, there is no disclosure relating to formation of a vesicle structure from normal treatment agent components alone. Moreover, there has been no mention of change or modification of hair surface properties.

Furthermore, a conventional phase inversion emulsification such as that described in Non-Patent Document 1 is a technique for forming a fine emulsion and is not disclosed as a technique for carrying out phase inversion emulsification in order to make an emulsion having a large particle size of more than 2 μm.

The present inventors have found that vesicles can be formed in water by additionally using a specific organic acid in combination with a specific tertiary amine and a specific branched fatty acid. It has also been found that a hair cosmetic employing the vesicle composition can exhibit the same or higher effects even if the content of the branched fatty acid is reduced compared with the conventional level.

Furthermore, it has been found that a vesicle composition that is formed from components (A), (B) and (C) and water and has a sufficient vesicle volume concentration can be produced by carrying out mixing while adding an aqueous phase to an oil phase containing a specific tertiary amine, a specific branched fatty acid, and a specific organic acid.

Moreover, the present inventors have found that the vesicles of the present invention maintain the average particle size of the vesicles formed at 2 μm or more and have a sufficient vesicle volume concentration, and the present invention has thus been accomplished.

That is, in accordance with the production method of the present invention, there can be provided a vesicle composition that is formed from components (A), (B) and (C) and water:
(A) a branched fatty acid represented by formula (1)

$$H_3C-\underset{R^1}{\overset{H}{C}}-(CH_2)_n-COOH \quad (1)$$

(In the Formula, $R^1$ represents a methyl group or an ethyl group, and n represents an integer of 5 to 36.);
(B) a tertiary amine represented by formula (2)

$$R^2-O-(CH_2)_3-\underset{R^4}{\overset{R^3}{N}} \quad (2)$$

(In the Formula, $R^2$ represents a straight-chain or branched alkyl or alkenyl group having 6 to 24 carbon atoms, $R^3$ and $R^4$ represent identical or different alkyl groups having 1 to 6 carbon atoms or -(AO)mH (AO represents an oxyalkylene group having 2 to 4 carbon atoms, m represents an integer of 1 to 6, the m AOs may be identical to or different from each other, and they may be in any sequence.);
(C) an organic acid having 1 to 10 carbon atoms.

In accordance with the vesicle composition of the present invention, even if the content of the branched fatty acid is reduced compared with a conventional hair cosmetic used in a "rinse-off form", the conforming feel when applying and smoothness during rinsing that have been realized by the conventional hair cosmetic can be maintained or improved.

Furthermore, even if it is used as a hair cosmetic used in a "non-rinse-off form", the smoothness when applying, ease of running the fingers through the hair, and manageability when drying can be maintained or improved.

DESCRIPTION OF EMBODIMENTS

The method for producing a vesicle composition of the present invention includes a step of completely dissolving an oil phase containing components (A), (B) and (C) below at a temperature that is equal to or higher than a melting point of the oil phase, and a step of carrying out mixing while adding an aqueous phase to the dissolved oil phase. Each of the components used is specifically explained below.
(A) Branched fatty acid
(B) Tertiary amine
(C) Organic acid having 1 to 10 carbon atoms First, component (A) is explained.
Component (A) used in the present invention is a branched fatty acid represented by formula (1).

$$H_3C-\underset{R^1}{\overset{H}{C}}-(CH_2)_n-COOH \quad (1)$$

(In the Formula, $R^1$ represents a methyl group or an ethyl group, and n represents an integer of 5 to 36.)

Among such branched fatty acids, n is preferably 5 to 35 (a total number of carbon atoms of the branched fatty acid being 9 to 40), more preferably 6 to 35 (the total number of carbon atoms of the branched fatty acid being 10 to 40), and even more preferably 6 to 19 (the total number of carbon atoms of the branched fatty acid being 10 to 24).

Specific examples thereof include 18-methyleicosanoic acid, 18-methylnonadecanoic acid, 14-methylpentadecanoic acid, 14-methylhexadecanoic acid, 15-methylhexadecanoic acid, 15-methylheptadecanoic acid, 16-methylheptadecanoic acid, 16-methyloctadecanoic acid, 17-methyloctadecanoic acid, and 17-methylnonadecanoic acid.

The branched fatty acid of component (A) may be separated and extracted from hair and the like in accordance with the description of LIPIDS, Vol. 23, No. 9, 878 to 881 (1988) or International Publication WO 98/30532, for example. The branched fatty acid of component (A) may also be synthesized in accordance with the description of Japanese Patent Publication NO. JP-A-4-173719 (Patent Document 1 above).

An extracted product includes an extract from lanolin, that is, a lanolin fatty acid and a salt thereof. Commercial lanolin fatty acids contain about 50 wt % of methyl branched long chain fatty acids called iso fatty acids and anteiso fatty acids. Specific examples thereof include 18-MEA manufactured by Croda Japan, SKLIRO manufactured by Croda Japan, and FA-NH manufactured by Nippon Fine Chemical.

With regard to the branched fatty acid of component (A), two or more types thereof may be used in combination. Moreover, a synthetic product and an extracted product may be used in combination.

Component (B) used in the present invention is a tertiary amine represented by formula (2).

$$R^2-O-(CH_2)_3-\underset{R^4}{\overset{R^3}{N}} \quad (2)$$

Here, $R^2$ is a straight-chain or branched alkyl or alkenyl group having 6 to 24 carbon atoms, and preferably a straight-chain or branched alkyl or alkenyl group having 12 to 24 carbon atoms, even more preferably 14 to 22 carbon atoms, and even more preferably a straight chain alkyl group, from the viewpoint of excellent slipperiness after drying.

$R^3$ and $R^4$ independently represent an alkyl group having 1 to 6 carbon atoms or -(AO)mH (AO represents an oxyalkylene group having 2 to 4 carbon atoms, m represents an integer of 1 to 6, the m AOs may be identical to or different from each other, and they may be in any sequence), and preferably represent an alkyl group having 1 to 6 carbon atoms or $-(CH_2CH_2O)mH$ (m represents an integer of 1 to 3, and even more preferably 1); it is more preferable that at least one of $R^3$ and $R^4$ is an alkyl group having 1 to 6 carbon atoms, preferably a methyl group or an ethyl group in particular, and it is more preferable that the two are the same, from the viewpoint of excellent slipperiness after drying.

Preferred specific examples of the tertiary amine include N,N-dimethyl-3-hexadecyloxypropylamine and N,N-dimethyl-3-octadecyloxypropylamine.

With regard to the tertiary amine of component (B), two or more types thereof may be used in combination.

Component (C) used in the present invention is an organic acid having 1 to 10 carbon atoms.

Specific examples thereof include a monocarboxylic acid such as acetic acid, propionic acid or capric acid; a dicarboxylic acid such as malonic acid, succinic acid, glutaric acid, adipic acid, maleic acid or fumaric acid; a hydroxycarboxylic acid such as glycolic acid, lactic acid, hydroxyacrylic acid, glyceric acid, malic acid, tartaric acid or citric acid; an aromatic carboxylic acid such as benzoic acid, salicylic acid or phthalic acid; and an acidic amino acid such as glutamic acid or aspartic acid. Among them, a hydroxycarboxylic acid and an acidic amino acid are preferable. As the hydroxycarboxylic acid, glycolic acid, citric acid, lactic acid, and malic acid are more preferable. As the acidic amino acid, glutamic acid is more preferable.

With regard to a combination of component (A), component (B) and component (C), the above-mentioned compounds may be combined as appropriate. The combination is not particularly limited. In case that component (A) is 18-methyleicosanoic acid and component (B) is N,N-dimethyl-3-octadecyloxypropylamine, it is preferable that, for example, component (C) is capric acid, lactic acid, malic acid or benzoic acid as a combination of component (A), component (B) and component (C).

Vesicles are formed from component (A), component (B), component (C) and water. In particular, a vesicle composition in which multilamellar vesicles (the so-called onion vesicles) formed from several double layers are dispersed in water is easily formed. A vesicle usually means a vesicular body in which the inner layer is hollow or an aqueous phase, but the multilamellar vesicle formed here includes one having a structure in which a part or the whole of the inner layer is an oil phase. Furthermore, the "vesicle" in the present application also includes a multilamellar vesicle.

The molar ratio (A)/(C) of component (A) and component (C) is 5/5 or more and preferably 7/3 or more, and is 9/1 or less and preferably 8/2, from the viewpoint of increasing the vesicle volume concentration in a vesicle dispersion.

Furthermore, the ratio of the acid equivalent of (A)+(C) and the base equivalent of (B) is 0.5 or more and preferably 0.6 or more, and is 2 or less and preferably 1.8 ore less, from the viewpoint of efficient contributions by component (A), component (B) and component (C) to formation of a vesicle.

Moreover, the total of component (A), component (B) and component (C) in the vesicle dispersion is preferably 1 to 20 wt %, and more preferably 1 to 15 wt %, from the viewpoint of storage stability and ease of handling of the vesicle dispersion.

The volume of the vesicles formed in the vesicle dispersion is preferably 4 times by volume or more relative to the content of component (A) in the vesicle composition, more preferably 6 times by volume or more, and even more preferably 8 times by volume or more, from the viewpoint to improve a conforming feel when applying and smoothness when rinsing.

Furthermore, a preferred mode of the vesicle dispersion is that the vesicle volume concentration is 20 to 80 vol %, preferably 30 to 80 vol % and, thereamong, even more preferably 30 to 60 vol %. When in this range the best improvements in storage stability of the vesicle dispersion, ease of handling, conforming feel and smoothness during rinsing are obtained.

The vesicle composition of the present invention is desirably in the form of vesicle dispersion (premix). This vesicle dispersion may be suitably produced by the following stages, that is,
(i) a step of completely dissolving an oil phase containing component (A), component (B) and component (C) at a temperature that is equal to or higher than the melting point of the oil phase, and
(ii) a step of carrying out mixing while adding an aqueous phase to the oil phase obtained.

In accordance with such a procedure, a vesicle composition having the aqueous phase as a continuous phase is obtained.

In step (i), it is necessary to completely dissolve the oil phase from the viewpoint of stable production. Here, "completely dissolve" means a state in which the oil phase has been dissolved so that no solids are present therein. Because of this, the oil phase is dissolved at a temperature that is equal to or higher than the melting point thereof, preferably at a temperature that is higher than the melting point of the oil phase by 5° C. or higher, and even more preferably at a temperature that is higher than the melting point of the oil phase by 10° C. or higher.

Furthermore, the oil phase is preferably in a uniformly mixed state. It is therefore preferable that in this step dissolution is carried out while the oil phase is mixed. The mixing method is not particularly limited, but for example it is preferable to carry out mixing by stirring.

In step (ii), the temperature at which the aqueous phase is added dropwise may be determined as appropriate by way of the temperature of the oil phase, the temperature of the aqueous phase added dropwise, and heating or cooling by means of a mixing device. Here, the "aqueous phase" employs purified water such as ion exchanged water or distilled water, and further may contain a water-soluble polyhydric alcohol as component (D) such as glycerol or dipropylene glycol. Furthermore, the temperature of the oil phase and the temperature of the aqueous phase added dropwise are preferably equal to or higher than the phase inversion temperature of the vesicles to be formed, from the viewpoint of efficient production of vesicles.

The vesicle volume concentration in the vesicle dispersion may be adjusted by the speed at which the aqueous phase is added dropwise to the oil phase and the stirring speed when the aqueous phase is added dropwise, and the particle size of the vesicles may be adjusted by the stirring speed (shear speed) after starting dropwise addition of the aqueous phase. The optimum values for the speed at which the aqueous phase is added dropwise to the oil phase and for the stirring speed at the time of dropwise addition vary according to the formulation or component ratio of the vesicle composition and the size and shape of a mixing vessel, but conditions under which mixing can be carried out uniformly is preferable in a state in which the viscosity is the highest during dropwise addition of the aqueous phase. If the aqueous phase is further added dropwise, the viscosity of the vesicle dispersion decreases, and the vesicle volume concentration decreases. The amount of aqueous phase added dropwise may be adjusted as appropriate while taking into consideration the storage stability and ease of handling of the vesicle dispersion.

Although the speed at which the aqueous phase is added dropwise to the oil phase may be selected appropriately as described above, it is desirable that dropwise addition is carried out over a period of 10 minutes or more for the purpose of increasing the vesicle volume concentration in the vesicle dispersion. The speed of dropwise addition is not particularly limited. For example, it is preferably added dropwise at 5 to 20 g/minute when the entire amount of the aqueous phase to be added dropwise is 600 g.

Furthermore, the method for producing a vesicle composition preferably includes, after step (ii),
(iii) a step of immediately carrying out cooling to not higher than the vesicle phase inversion temperature after drop completion of the aqueous phase, from the viewpoint of stability of the vesicle composition.

With regard to the vesicle volume concentration in the vesicle composition, the precise volume of the vesicles passing through the aperture can be determined by measuring a change in the electric resistance, voltage or current between two electrodes placed across the aperture when the vesicle composition is dispersed in an electrolyte solution, and the vesicles floating in the electrolyte solution pass through a region marked off by a narrow hole called an aperture. Measurement may be carried out using a particle size distribution measuring device employing such a principle, for example, a Multisizer™ 4 manufactured by Beckman Coulter, Inc. or a CDA-1000X manufactured by Sysmex Corporation.

In case that the vesicle has a spherical shape, the average particle size is 2 μm or more, preferably 3 μm or more, and more preferably 5 μm or more, and is 20 μm or less, preferably 18 μm or less, and more preferably 15 μm or less, from the viewpoint of further improving the conforming feel when applying to hair. Here, the average particle size may be measured using a particle size distribution measuring device used in the above-mentioned measurement of vesicle volume concentration such as a Multisizer™ 4 manufactured by Beckman Coulter, Inc. or a CDA-1000X manufactured by Sysmex Corporation, or from a volume distribution obtained by converting from an intensity distribution of scattered light obtained by applying laser light to vesicles moving in a flow cell in a circulation system and measured using a laser diffraction particle size distribution measuring device such as a SALD2100 manufactured by Shimadzu Corporation or an LA-920 manufactured by Horiba, Ltd. Measurement is desirably carried out at room temperature (15° C. to 30° C.)

The vesicle composition of the present invention may further contain (D) a polyhydric alcohol.

Specific examples of component (D) include ethylene glycol, diethylene glycol, propylene glycol, dipropylene glycol, and glycerol.

The content of component (D) is preferably 0.5 to 60 wt % relative to the entire vesicle composition, and more preferably 1 to 50 wt %, from the viewpoint of the storage stability of the vesicle composition.

In the above-mentioned stage (i) when adding component (D), component (D) may be added to the oil phase after dissolving the oil phase containing component (A), component (B) and component (C) at a temperature that is equal to or higher than the melting point of the oil phase. Alternatively, in the above-mentioned stage (i), an oil phase may be obtained in which an oil phase containing component (A), component (B), component (C) and component (D) has been dissolved at a temperature that is equal to or higher than the melting point of the oil phase so that no solids are present. A vesicle dispersion having a high vesicle volume concentration and high storage stability may be obtained through stage (ii) in which mixing is carried out while adding an aqueous phase to the obtained oil phase after stage (i). Moreover, it is preferable to carry out stage (iii) in which immediate cooling to not higher than the vesicle phase inversion temperature is carried out after drop completion of the aqueous phase, from the viewpoint of vesicle storage stability.

Furthermore, the oil phase may be added an optional component as long as production of the vesicles of the present invention is not prevented. Examples of said optional component include, without limitation, various types of extracts and antioxidants. The optional component that can be added to the oil phase is not more than 1% of the oil phase, from the viewpoint of stable production of a vesicle composition.

The aqueous phase may contain an optional component as long as production of the vesicles of the present invention is not prevented. Examples of said optional component include, but not particularly limited to, various types of extracts and preservatives. The optional component that can be added to the aqueous phase is not more than 0.1% of the aqueous phase, from the viewpoint of stable production of a vesicle composition.

When producing the vesicle composition, an aqueous phase is added dropwise to an oil phase in a shear-mixed state. The mixing device is not particularly limited as long as shear-mixing is possible. When the viscosity becomes high during addition of an aqueous phase, a device that can mix a high viscosity substance is preferable, for example, an Agi-Homo mixer or a T.K. Combimix manufactured by PRIMIX Corporation, a vacuum emulsion stirring vessel manufactured by Mizuho Industrial Co., Ltd., a MaxBlend stirring vessel manufactured by Sumitomo Heavy Industries, Ltd. or a Supermix stirring vessel manufactured by Satake Chemical Equipment MFG., Ltd. The stirring speed is not particularly limited, but it is preferable to carry out stirring at 50 to 100 rpm, for example.

Although it has not been confirmed, it is surmised that in accordance with the vesicles obtained by such a production method of the present invention, the properties on the hair surface can be suitably changed due to the structure easily changing from a vesicle to a film form when applied to the hair.

Furthermore, a conventional vesicle structure, as described in Patent Document 3, is constructed by interposition of a specific lipid such as a sterol or a phospholipid. On the other hand, the present invention can form a vesicle composition without a sterol or a phospholipid being contained. That is, it is a new finding in terms of it being possible to form a vesicle structure from components that are conventionally used in a hair cosmetic such as a rinse or a conditioner. Therefore, the present invention provides a novel formulation in the present field.

The hair cosmetic of the present invention contains the above-mentioned vesicle composition.

The content of the vesicle composition in the hair cosmetic as the amount of branched fatty acid is preferably 0.01 to 5 wt %, and more preferably 0.05 to 2 wt % as component (A) constituting the vesicle, from the viewpoint of imparting a conforming feel when applying and smoothness during rinsing. Even if the content of an effective component in such a hair cosmetic is reduced compared with the conventional hair cosmetic, the softness, smoothness, moist feel and suppleness that have been realized by a conventional hair cosmetic can be maintained or improved.

Examples of such a hair cosmetic include a conditioner, a rinse, a treatment and a shampoo. A conditioner, a rinse and a treatment are preferable as a particularly effective hair cosmetic. These hair cosmetics may be used either in a form in which a hair cosmetic is rinsed off after applying or in a form in which it is not rinsed off.

The hair cosmetic containing the vesicle composition is obtained by mixing the vesicle composition of the present invention with a hair cosmetic that has been prepared separately by a standard method. The hair cosmetic that has been prepared by a general method means a general hair cosmetic including a surfactant, a silicone, an oil-based component, for example. This may be prepared by any method.

A formulation and a production method for the hair cosmetic are not particularly limited, and for example, it is obtained by adding a heated and stirred aqueous phase to an oil phase containing a cationic surfactant, a higher alcohol and an emulsified silicone, and carrying out emulsification.

A method for formulating the present vesicle composition into a general hair cosmetic is not particularly limited, but it is desirable to carry out formulation at a temperature that is not higher than the vesicle gel transition temperature, from the viewpoint of vesicle stability. In this way, the hair cosmetic that maintains the structure of the vesicle composition can be obtained.

EXAMPLES

Example 1

An emulsification device (T.K. Agi-Homo Mixer, Primix Corporation) was charged with 28.00 g of 18-MEA (a mixture of fatty acid and branched fatty acid containing 18-methyleicosanoic acid, average molecular weight: 364.3, melting point 35 to 55° C.) manufactured by Croda Japan, 1.92 g of Musashino lactic acid 90 (lactic acid, purity 90%, molecular weight: 90.08, melting point 18° C.) manufactured by Musashino Chemical Laboratory, Ltd., 37.94 g of Farmin DM E-80 (N,N-dimethyloctadecyloxypropylamine, purity 90%, molecular weight 355.63, melting point 29° C.) manufactured by Kao Corporation, and 84 g of DPG-RF (dipropylene glycol, melting point −40° C.) manufactured by ADEKA, and then hot water was charged into a jacket so that the vessel internal temperature became 80° C. The starting materials were completely dissolved by stirring using a paddle blade (80 rpm). 648.14 g of ion exchanged water heated to 80° C. as the aqueous phase was added dropwise to the resulting oil phase over 60 minutes at a constant speed, and emulsification was carried out at 80° C. Subsequently, cooling to 30° C. or below was carried out by a coolant at 5° C. The vesicle composition obtained in this way was defined as a premix. An emulsification method in which an aqueous phase is added dropwise while stirring an oil phase is generally called phase inversion emulsification. When the gel transition temperature of this vesicle composition was measured using a differential scanning calorimeter (DSC), it was found to be 51.8° C.

Table 1 shows conditions for production of the premix and the amount (g) of each component converted on the basis of 10.00 g of the premix.

A rinse was formulated using the premix prepared above, which was the vesicle composition. Rinses prepared in Examples 1 to 11 and Comparative Examples 1 to 4 were hair cosmetics for use in a rinse-off form.

A 500 mL beaker was charged with 301.40 g of ion exchanged water and 2.36 g of Musashino lactic acid 90 as the aqueous phase, and heated to 55° C. while stirring with a propeller. Subsequently, an oil phase consisting of 9.29 g of Farmin DM E-80, 21.00 g of Kalcol 8098 (stearyl alcohol, purity 98%) manufactured by Kao Corporation, and 5.95 g of DPG-RF (the same as above) was dissolved uniformly at 80° C., and then the resulting oil phase was added to the aqueous phase, and emulsification was carried out by stirring at 300 rpm for 10 minutes. Leaving to cool to 35° C. or below provided a base rinse, and 10.00 g of the above-mentioned premix was then added thereto, to provide a rinse.

Comparative Example 1

An emulsification device (T.K. Agi-Homo Mixer) manufactured by Primix Corporation was charged with 648.14 g of ion exchanged water as an aqueous phase, and then hot water was charged into a jacket of the emulsification device while stirring using a paddle blade (80 rpm). The vessel internal temperature was adjusted to 80° C. Subsequently, 28.00 g of 18-MEA (a mixture of fatty acid and branched fatty acid containing 18-methyleicosanoic acid, average molecular weight: 364.3) manufactured by Croda Japan, 1.92 g of Musashino lactic acid 90 (lactic acid, purity 90%, molecular weight: 90.08) manufactured by Musashino Chemical Laboratory, Ltd., 37.94 g of Farmin DM E-80 (N,N-dimethyloctadecyloxypropylamine, purity 90%, molecular weight 355.63) manufactured by Kao Corporation, and 84 g of DPG-RF (dipropylene glycol) manufactured by ADEKA were placed in a beaker, and completely dissolved in a water bath at 80° C. while stirring to provide an oil phase. The resulting oil phase was added dropwise at a constant speed over 60 minutes to the aqueous phase in the emulsification device while stirring with a paddle blade. Subsequently, cooling to 30° C. or below was carried out by a coolant at 5° C. A vesicle composition obtained in this way was defined as a premix. An emulsification method in which an oil phase is added dropwise while stirring an aqueous phase is generally called normal phase emulsification. Table 1 shows conditions for production of the premix and the amount (g) of each component converted on the basis of 10.00 g of the premix.

Subsequently, in order to carry out evaluation in the same manner as in Example 1, formulation of a rinse was carried out.

A 500 mL beaker was charged with 301.40 g of ion exchanged water and 2.36 g Musashino lactic acid 90 as an aqueous phase, and heated to 55° C. while stirring with a propeller. Subsequently, an oil phase consisting of 9.29 g of Farmin DM E-80, 21.00 g of Kalcol 8098 (stearyl alcohol, purity 98%) manufactured by Kao Corporation, and 5.95 g of DPG-RF (the same as above) was dissolved uniformly at 80° C., and then the resulting oil phase was added to the aqueous phase, and emulsification was carried out by stirring at 300 rpm for 10 minutes. Leaving to cool to 35° C. or below resulted in a base rinse, and 10.00 g of the above-mentioned premix was then added thereto, resulting in a rinse.

Example 2

A premix and a rinse were prepared in the same manner as in Example 1 except that oil phase components were dissolved at a vessel internal temperature of the emulsification device of 45° C., and the temperature of ion exchanged water added dropwise was 45° C. When the gel transition temperature of the vesicles thus formed was measured using a differential scanning calorimeter (DSC), it was found to be 51.6° C.

Example 3

A premix and a rinse were prepared in the same manner as in Example 1 except that particle size was controlled by applying shear to the premix preparation by means of a Homo-Mixer at 7000 rpm for 30 minutes.

Comparative Example 2

A 500 mL beaker was charged with 309.50 g of ion exchanged water and 2.38 g of Musashino lactic acid 90 as an aqueous phase, and heated to 55° C. while stirring with a propeller. The resulting aqueous phase was added an oil phase consisting of 0.35 g of 18-MEA, 13.19 g of Farmin DM E-80, 7.00 g of DPG-RF and 21.00 g of Kalcol 8098, which had been uniformly dissolved in advance at 80° C., and emulsification was carried out by stirring at 300 rpm for 10 minutes. Subsequently, leaving to cool to 35° C. or below resulted in a rinse.

Comparative Example 3

A rinse was prepared in the same manner as in Comparative Example 2 except that ion exchanged water was 308.10 g, and 1.40 g of benzyl alcohol (purity 99.9%) manufactured by Sun Chemical Company Ltd. was added to the oil phase.

Example 4

A premix and a rinse were prepared in the same manner as in Example 1 except that the amount of DPG-RF in 10.00 g of the premix was 0.00 g, and the amount of DPG-RF during preparation of a base rinse was 7.00 g.

Example 5

A premix and a rinse were prepared in the same manner as in Example 1 except that the amount of Farmin DM E-80 in 10.00 g of the premix was 0.95 g and the amount of Farmin DM E-80 during preparation of a base rinse was 8.82 g.

Example 6

A premix and a rinse were prepared in the same manner as in Example 1 except that the amount of Farmin DM E-80 in 10.00 g of the premix was 0.24 g, and the amount of Farmin DM E-80 during preparation of a base rinse was 9.53 g.

Example 7

A premix and a rinse were prepared in the same manner as in Example 1 except that the amount of lactic acid in 10.00 g of the premix was 0.10 g, Farmin DM E-80 was 0.76 g, the amount of lactic acid during preparation of a base rinse was 2.28 g, and Farmin DM E-80 was 9.01 g.

Comparative Example 4

A premix and a rinse were prepared in the same manner as in Example 1 except that the amount of lactic acid in 10.00 g of the premix was 0.00 g, Farmin DM E-80 was 0.38 g, the amount of lactic acid during preparation of a base rinse was 2.38 g, and Farmin DM E-80 was 9.39 g.

Example 8

A premix and a rinse were prepared in the same manner as in Example 1 except that the amount of Farmin DM E-80 in 10.00 g of the premix was 1.90 g and the amount of Farmin DM E-80 during preparation of a base rinse was 7.87 g.

Example 9

A premix and a rinse were prepared in the same manner as in Example 1 except that the amount of Farmin DM E-80 in 10.00 g of the premix was 0.12 g and the amount of Farmin DM E-80 during preparation of a base rinse was 9.65 g.

Example 10

A premix and a rinse were prepared in the same manner as in Example 1 except that 0.02 g of lactic acid in 10.00 g of the premix was changed to 0.05 g of capric acid (reagent grade, 99% crystals) manufactured by Wako Pure Chemical Industries, Ltd. and ion exchanged water was 8.08 g.

Example 11

A premix and a rinse were prepared in the same manner as in Example 1 except that 0.02 g of lactic acid in 10.00 g of the premix was changed to 0.04 g of benzoic acid (top reagent grade) manufactured by Sigma Aldrich Japan and ion exchanged water was 8.09 g.

Method for Evaluating Premix (1) Vesicle volume concentration in the premix was measured using a Multisizer™ 4 manufactured by Beckman Coulter, Inc. at 25° C.

(2) Average particle size of the vesicles in the premix was measured by a circulation method using a SALD2100 laser diffraction particle size distribution measuring device manufactured by Shimadzu Corporation. With regard to the average particle size, median diameter ($D_{50}$) on a volume basis was used.

(3) Stability of the premix was evaluated by change in viscosity (B type viscometer, rotor No. 2, 30 rpm, 1 minute) manufactured by Tokyo Keiki Co., Ltd. after being subjected to thermal aging of 50° C. for 1 month.

Method for Evaluating Rinse 20 g of Japanese female hair (about 15.20 cm) that had been subjected to a cosmetic treatment such as a cold perm or bleaching was bundled and washed using a shampoo. 2 g of the rinse prepared in Examples 1 to 11 and Comparative Examples 1 to 4 was applied uniformly to this hair and rinsed off using running water for 30 seconds. During this period, "conforming feel when applying" and "smoothness during rinsing" were subjected to sensory evaluation.

Evaluation was carried out by 5 expert panelists using 5 grades, and the average value thereof was used. When the average score was 3 or more, it was assessed as a pass.

Evaluation Criteria

5: both conforming feel when applying and smoothness during rinsing were excellent
4: both conforming feel when applying and smoothness during rinsing were good
3: one of conforming feel when applying and smoothness during rinsing was good
2: one of conforming feel when applying and smoothness during rinsing was poor
1: both conforming feel when applying and smoothness during rinsing were poor

TABLE 1

|  |  |  | Example 1 | Comp. Ex. 1 | Example 2 | Example 3 | Comp. Ex. 2 | Comp. Ex. 3 | Example 4 | Example 5 |
|---|---|---|---|---|---|---|---|---|---|---|
| Premix | (A) 18-MEA | [g] | 0.35 | 0.35 | 0.35 | 0.35 | — | — | 0.35 | 0.35 |
|  | (C) Musashino lactic acid 90 | [g] | 0.02 | 0.02 | 0.02 | 0.02 | — | — | 0.02 | 0.02 |
|  | (C) Capric acid | [g] | — | — | — | — | — | — | — | — |
|  | (C) Benzoic acid | [g] | — | — | — | — | — | — | — | — |
|  | (B) Farmin DM E-80 | [g] | 0.47 | 0.47 | 0.47 | 0.47 | — | — | 0.47 | 0.95 |
|  | DPG-RF | [g] | 1.05 | 1.05 | 1.05 | 1.05 | — | — | — | 1.05 |
|  | Ion exchanged water | [g] | 8.11 | 8.11 | 8.11 | 8.11 | — | — | 9.16 | 7.63 |
|  | Premix Total | [g] | 10.00 | 10.00 | 10.00 | 10.00 |  |  | 10.00 | 10.00 |

TABLE 1-continued

| | | | | | | | | | | |
|---|---|---|---|---|---|---|---|---|---|---|
| Premix production conditions | Degree of neutralization: ((A) + (C))/(B) | (Mol ratio) | 1.00 | 1.00 | 1.00 | 1.00 | — | — | 1.00 | 0.50 |
| | (A):(C) Emulsification method | (Mol ratio) | 8:2 Phase inversion | 8:2 Normal phase | 8:2 Phase inversion | 8:2 Phase inversion | — | — | 8:2 Phase inversion | 8:2 Phase inversion |
| | Emulsification temperature | [° C.] | 80 | 80 | 45 | 80 | — | — | 80 | 80 |
| | Homo Mixer | | — | — | — | 7000 rpm × 30 min | — | — | — | — |
| Rinse | Ion exchanged water | [g] | 301.40 | 301.40 | 301.40 | 301.40 | 309.50 | 308.10 | 300.35 | 301.87 |
| | Musashino lactic acid 90 | [g] | 2.36 | 2.36 | 2.36 | 2.36 | 2.38 | 2.38 | 2.36 | 2.36 |
| | Farmin DM E-80 | [g] | 9.29 | 9.29 | 9.29 | 9.29 | 9.77 | 9.77 | 9.29 | 8.82 |
| | Kalcol 8098 | [g] | 21.00 | 21.00 | 21.00 | 21.00 | 21.00 | 21.00 | 21.00 | 21.00 |
| | DPG-RF | [g] | 5.95 | 5.95 | 5.95 | 5.95 | 7.00 | 7.00 | 7.00 | 5.95 |
| | Benzyl alcohol | [g] | — | — | — | — | — | 1.40 | — | — |
| | Premix | [g] | 10.00 | 10.00 | 10.00 | 10.00 | — | — | 10.00 | 10.00 |
| | 18-MEA | [g] | — | — | — | — | 0.35 | 0.35 | — | — |
| | Rinse total | | 350.00 | 350.00 | 350.00 | 350.00 | 350.00 | 350.00 | 350.00 | 350.00 |
| Evaluation | (1) Vesicle volume concentration | [vol %] | 42.8 | 10.6 | 46.3 | 35.2 | — | — | 31.5 | 27.2 |
| | Vesicle volume/(A) 18MEA volume | [—] | 11.0 | 2.7 | 11.9 | 9.1 | — | — | 8.1 | 7.0 |
| | (2) Av. particle size ($D_{50}$) | [μm] | 7.8 | 4.1 | 4.5 | 0.8 | — | — | 8.5 | 4.2 |
| | (4) Premix initial viscosity | [mPa·s] | 46 | 171 | 157 | 30 | — | — | 300 | 42 |
| | (4) Premix viscosity after storage | [mPa·s] | 150 | 380 | 320 | 140 | — | — | 3,500 | 140 |
| | Expert panelist A | | 5 | 2 | 4 | 3 | 1 | 1 | 3 | 3 |
| | Expert panelist B | | 5 | 3 | 4 | 4 | 1 | 2 | 4 | 4 |
| | Expert panelist C | | 5 | 2 | 3 | 2 | 1 | 1 | 4 | 3 |
| | Expert panelist D | | 5 | 2 | 4 | 3 | 1 | 1 | 3 | 4 |
| | Expert panelist E | | 5 | 2 | 3 | 3 | 1 | 1 | 4 | 4 |
| | Average points | | 5.0 | 2.2 | 3.6 | 3.0 | 1.0 | 1.2 | 3.6 | 3.6 |

| | | | Example 6 | Example 7 | Comp. Ex. 4 | Example 8 | Example 9 | Example 10 | Example 11 |
|---|---|---|---|---|---|---|---|---|---|
| Premix | (A) 18-MEA | [g] | 0.35 | 0.35 | 0.35 | 0.35 | 0.35 | 0.35 | 0.35 |
| | (C) Musashino lactic acid 90 | [g] | 0.02 | 0.10 | — | 0.02 | 0.02 | — | — |
| | (C) Capric acid | [g] | — | — | — | — | — | 0.05 | — |
| | (C) Benzoic acid | [g] | — | — | — | — | — | — | 0.04 |
| | (B) Farmin DM E-80 | [g] | 0.24 | 0.76 | 0.38 | 1.90 | 0.12 | 0.47 | 0.47 |
| | DPG-RF | [g] | 1.05 | 1.05 | 1.05 | 1.05 | 1.05 | 1.05 | 1.05 |
| | Ion exchanged water | [g] | 8.34 | 7.74 | 8.22 | 6.68 | 8.46 | 8.08 | 8.09 |
| | Premix Total | [g] | 10.00 | 10.00 | 10.00 | 10.00 | 10.00 | 10.00 | 10.00 |
| Premix production conditions | Degree of neutralization: ((A) + (C))/(B) | (Mol ratio) | 2.00 | 1.00 | 1.00 | 0.25 | 4.00 | 1.00 | 1.00 |
| | (A):(C) Emulsification method | (Mol ratio) | 8:2 Phase inversion | 5:5 Phase inversion | 10:0 Phase inversion | 8:2 Phase inversion | 8:2 Phase inversion | 8:2 Phase inversion | 8:2 Phase inversion |
| | Emulsification temperature | [° C.] | 80 | 80 | 80 | 80 | 80 | 80 | 80 |
| | Homo Mixer | | — | — | — | — | — | — | — |
| Rinse | Ion exchanged water | [g] | 301.17 | 301.76 | 301.28 | 302.82 | 301.04 | 301.40 | 301.40 |
| | Musashino lactic acid 90 | [g] | 2.36 | 2.28 | 2.38 | 2.36 | 2.36 | 2.36 | 2.36 |
| | Farmin DM E-80 | [g] | 9.53 | 9.01 | 9.39 | 7.87 | 9.65 | 9.29 | 9.29 |
| | Kalcol 8098 | [g] | 21.00 | 21.00 | 21.00 | 21.00 | 21.00 | 21.00 | 21.00 |
| | DPG-RF | [g] | 5.95 | 5.95 | 5.95 | 5.95 | 5.95 | 5.95 | 5.95 |
| | Benzyl alcohol | [g] | — | — | — | — | — | — | — |
| | Premix | [g] | 10.00 | 10.00 | 10.00 | 10.00 | 10.00 | 10.00 | 10.00 |
| | 18-MEA | [g] | — | — | — | — | — | — | — |
| | Rinse total | | 350.00 | 350.00 | 350.00 | 350.00 | 350.00 | 350.00 | 350.00 |
| Evaluation | (1) Vesicle volume concentration | [vol %] | 28.4 | 25.8 | 5.2 | 17.6 | 16.3 | 31.9 | 22.7 |
| | Vesicle volume/(A) 18MEA volume | [—] | 7.3 | 6.6 | 1.3 | 4.5 | 4.2 | 8.2 | 5.8 |
| | (2) Av. particle size ($D_{50}$) | [μm] | 6.7 | 7.5 | 4.5 | 5.2 | 6.5 | 12.2 | 5.8 |
| | (4) Premix initial viscosity | [mPa·s] | 49 | 46 | 420 | 370 | 45 | 210 | 150 |

TABLE 1-continued

|  |  | | | | | | | |
|---|---|---|---|---|---|---|---|---|
| (4) Premix viscosity after storage | [mPa · s] | 150 | 150 | 530 | 450 | 150 | 330 | 230 |
| Expert panelist A | | 3 | 3 | 1 | 3 | 3 | 3 | 3 |
| Expert panelist B | | 4 | 4 | 2 | 3 | 4 | 4 | 4 |
| Expert panelist C | | 3 | 3 | 1 | 3 | 3 | 4 | 4 |
| Expert panelist D | | 3 | 3 | 2 | 3 | 3 | 4 | 3 |
| Expert panelist E | | 4 | 3 | 1 | 3 | 3 | 4 | 3 |
| Average points | | 3.4 | 3.2 | 1.4 | 3.0 | 3.2 | 3.8 | 3.4 |

Example 12

A treatment for use in a non-rinse-off form was formulated using the premix, which was the vesicle composition prepared in Example 1.

A 500 mL beaker was charged with 323.68 g of ion exchanged water, 0.69 g of Musashino lactic acid 90, and 10.50 g of Japanese Pharmacopoeia conc. glycerol (glycerol, purity 98%) manufactured by Kao Corporation as an aqueous phase and heated to 55° C. while stirring with a propeller. Subsequently, an oil phase consisting of 1.40 g of Quartamin 2285E (ethanol solution of behenyltrimethylammonium chloride, purity 80%, molecular weight 404.16) manufactured by Kao Corporation and 8.75 g of Kalcol 6850 (cetostearyl alcohol, purity 97%) manufactured by Kao Corporation was dissolved uniformly at 80° C., and then the resulting oil phase is added to the aqueous phase, and emulsification was carried out by stirring at 300 rpm for 10 minutes. Subsequently, leaving to cool to 35° C. or below resulted in a base conditioner. The base conditioner was added 4.97 g of the premix which was the vesicle composition prepared in Example 1, to provide a treatment for use in a non-rinse-off form.

Comparative Example 5

A 500 mL beaker was charged with 327.73 g of ion exchanged water, 0.70 g of Musashino lactic acid 90, and 10.50 g of Japanese Pharmacopoeia conc. glycerol as an aqueous phase, and heated to 55° C. while stirring with a propeller, and then was added. an oil phase consisting of 0.17 g of 18-MEA, 0.23 g of Farmin DM E-80, 1.40 g of Quartamin 2285E (ethanol solution of behenyltrimethylammonium chloride, purity 80%, molecular weight 404.16) manufactured by Kao Corporation, 0.52 g of DPG-RF, and 8.75 g of Kalcol 6850 that had been dissolved uniformly in advance at 80° C., and emulsification was carried out by stirring at 300 rpm for 10 minutes. Subsequently, leaving to cool to 35° C. or below resulted in a treatment for use in a non-rinse-off form.

Method for Evaluating Treatment for Use in a Non-Rinse-Off Form
Preparation of Bundle of Damaged Hair A bundle of hair having a length of 15 cm, a width of 3 cm, and a hair weight of 3 g was prepared using Japanese female hair that had not been subjected to a chemical treatment such as perming or hair coloring. Subsequently, this bundle of hair was subjected to a bleaching treatment (Puritia Funwari Awa Color High Bleach) manufactured by Kao Corporation twice, to provide a bundle of damaged hair.

Method for Treating a Bundle of Hair

The bundle of damaged hair was washed with a plain shampoo (Kyureru shampoo) manufactured by Kao Corporation, and then dried to remove water with a dry towel. This bundle of damaged hair was coated uniformly with 0.3 g of the hair treatment described in Example 12 and Comparative Example 5, and "smoothness" and "ease of running the fingers through (slipperiness)" when applied to wet hair were evaluated. Subsequently, the bundle of hair that had been combed for 5 minutes using a rattail comb while applying hot air at 70° C. from a dryer was subjected to evaluation in terms of "smoothness" and "manageability" after finishing with a dryer.

Evaluation was carried out by 5 expert panelists using 5 grades, and the average value thereof was used. Evaluation was carried out when applied to wet hair and after finishing with a dryer, and when the average score was 3 or more in both evaluations it was assessed as a pass.

Evaluation Criteria
When Applied to Wet Hair
5: both smoothness and ease of running the fingers through when applied wet were excellent
4: both smoothness and ease of running the fingers through when applied wet were good
3: one of smoothness and ease of running the fingers through when applied wet was good
2: one of smoothness and ease of running the fingers through when applied wet was poor
1: both smoothness and ease of running the fingers through were when applied wet poor
After Finishing with Dryer
5: both smoothness and manageability after finishing with dryer were excellent
4: both smoothness and manageability after finishing with dryer were good
3: one of smoothness and manageability after finishing with dryer was good
2: one of smoothness and manageability after finishing with dryer was poor
1: both smoothness and manageability after finishing with dryer were poor

TABLE 2

|  | Example 12 | Comp. Ex. 5 |
|---|---|---|
| Starting material name | | |
| Quartamin 2285E | 1.40 | 1.40 |
| Farmin DM E-80 | — | 0.23 |
| Kalcol 6850 | 8.75 | 8.75 |
| Glycerol | 10.50 | 10.50 |
| Musashino lactic acid 90 | 0.69 | 0.70 |
| Premix | 4.97 | — |
| 18-MEA | — | 0.17 |
| DPG-RF | — | 0.52 |
| Ion exchanged water | 323.69 | 327.73 |
|  | 350.00 | 350.00 |
| Evaluation (when applying to wet hair) | | |
| Expert panelist A | 5 | 2 |
| Expert panelist B | 5 | 2 |
| Expert panelist C | 5 | 2 |
| Expert panelist D | 5 | 2 |
| Expert panelist E | 5 | 2 |

TABLE 2-continued

|  | Example 12 | Comp. Ex. 5 |
|---|---|---|
| Average points | 5 | 2 |
| Evaluation (after drying with dryer) | | |
| Expert panelist A | 5 | 2 |
| Expert panelist B | 4 | 1 |
| Expert panelist C | 4 | 2 |
| Expert panelist D | 5 | 1 |
| Expert panelist E | 5 | 1 |
| Average points | 4.6 | 1.4 |

The invention claimed is:

1. A vesicle composition formed from components (A), (B) and (C) and water and having an aqueous phase as a continuous phase, a vesicle being contained in the vesicle composition at 4 times by volume or more relative to a content of component (A):

(A) a branched fatty acid represented by formula (1)

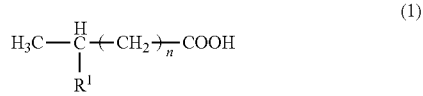

wherein the formula (1), $R^1$ represents a methyl group or an ethyl group, and n represents an integer of 5 to 36;

(B) a tertiary amine represented by formula (2)

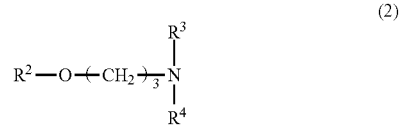

wherein the formula (2), $R^2$ represents a straight-chain or branched alkyl or alkenyl group having 6 to 24 carbon atoms, $R^3$ and $R^4$ represent identical or different alkyl groups having 1 to 6 carbon atoms or -(AO)mH wherein AO represents an oxyalkylene group having 2 to 4 carbon atoms, m represents an integer of 1 to 6, the m AOs may be identical to or different from each other, and they may be in any sequence;

(C) an organic acid having 1 to 10 carbon atoms;

wherein the vesicle composition is produced by a method comprising a step of a phase inversion emulsification;

an optional component that can be added to the oil phase is not more than 1% of the oil phase;

the vesicle component does not include sterols; and when the vesicle is spherical shape, an average particle size is 3-20 μm.

2. The vesicle composition according to claim 1, further comprising (D) a polyhydric alcohol.

* * * * *